(12) United States Patent
McDonnell et al.

(10) Patent No.: US 7,238,793 B2
(45) Date of Patent: Jul. 3, 2007

(54) ESTROGEN RECEPTOR MODULATORS

(75) Inventors: Donald P. McDonnell, Chapel Hill, NC (US); John D. Norris, Raleigh, NC (US); Daju Fan, Chapel Hill, NC (US)

(73) Assignee: Duke University, Durham, NC (US)

( * ) Notice: Subject to any disclaimer, the term of this patent is extended or adjusted under 35 U.S.C. 154(b) by 674 days.

(21) Appl. No.: 10/108,992

(22) Filed: Mar. 29, 2002

(65) Prior Publication Data

US 2002/0141984 A1    Oct. 3, 2002

Related U.S. Application Data

(60) Provisional application No. 60/279,455, filed on Mar. 29, 2001.

(51) Int. Cl.
    *C07H 21/00* (2006.01)
(52) U.S. Cl. .................. 536/23.1; 435/320.1; 435/325; 435/69.1
(58) Field of Classification Search ..................... None
    See application file for complete search history.

(56) References Cited

U.S. PATENT DOCUMENTS 6,020,164 A * 2/2000 Bandman et al. .......... 435/69.1

OTHER PUBLICATIONS

Bowie et al (Science, 1990, 247:1306-1310).*
Boehringer Mannheim Biochemicals, 1994 Catalog, p. 93.*
Database NCBI Online (Bethesda, MD, USA) Entrez Nucleotide, Accession No. AL009266, Jan. 25, 1999—see attached Swiss-Prot 043251.
Norris et al, "A Negative Coregulator for the Human ER", Mol. Endocrinol. 16(3):459-468 (2002).
Robyr et al, "Nuclear Hormone Receptor Coregulators In Action: Diversity For Shared Tasks", Mol. Endocrinol. 14(3):329-347 (2000).
Underwood et al, "Homologues of the *Caenorhabditis elegans* Fox-1 Protein Are Neuronal Splicing Regulators in Mammals", Molecular and Cellular Biology 25(22):10005-10016 (2005).
Li et al, "Cell type and culture condition-dependent alternative splicing in human breast cancer cells revealed by splicing-sensitive microarrays", Cancer Res. 66(4):1990-1999 (2006)—Abstract.
Nakahata and Kawamoto, "Tissue-dependent isoforms of mammalian Fox-1 homologs are associated with tissue-specific splicing activities", Nucleic Acids Research 33(7):2078-2089 (2005).

* cited by examiner

*Primary Examiner*—Shanon Foley
*Assistant Examiner*—Laura B Goddard
(74) *Attorney, Agent, or Firm*—Nixon & Vanderhye P.C.

(57) ABSTRACT

The present invention relates to an estrogen receptor co-regulator and to antibodies specific therefor. The invention further relates to methods of screening test compounds for their suitability as estrogen receptor modulators and to methods of using same in disease treatment.

10 Claims, 6 Drawing Sheets

Figure 1

```
  1   M Q N E P L T P G Y H G F P A R D S Q G N Q E P T T
 27   T P D A M V Q P F T T I P F P P P P Q N G I P T E Y
 53   G V P H T Q D Y A G Q T G E H N L T L Y G S T Q A H
 79   G E Q S S N S P S T Q N G S L T T E G G A Q T D G Q
                                                    RNP-2
105   Q S Q T Q S S E N S E S K S T P K R |L H V S N I| P F
131   R F R D P D L R Q M F G Q F G K I L D V E I I F N E
              RNP-1
157   R G S |K G F G F V T F| E N S A D A D R A R E K L H G
183   T V V E G R K I E V N N A T A R V M T N K K M V T P
209   Y A N G W K L S P V V G A V Y G P E L Y A A S S F Q
235   A D V S L G N D A A V P L S G R G G I N T Y I P L I
261   S L P L V P G F P Y P T A A T T A A A F R G A H L R
287   G R G R T V Y G A V R A V P P T A I P A Y P G V V Y
313   Q D G F Y G A D L Y G G Y A A Y R Y A Q P A T A T A
339   A T A A A A A A A A Y S D G Y G R V Y T A D P Y H A
365   L A P A A S Y G V G A V A S L Y R G G Y S R F A P Y
```

ESTROGEN RECEPTOR MODULATORS

This application claims benefit to Provisional Application No. 60/279,455, filed Mar. 29, 2001, now abandoned, the entire content of which is incorporated herein by reference.

This invention was made with Government support under Grant No. DK48807 awarded by the National Institutes of Health. The Government has certain rights in the invention.

TECHNICAL FIELD

The present invention relates to an estrogen receptor co-regulator and to antibodies specific therefor. The invention further relates to methods of screening test compounds for their suitability as estrogen receptor modulators and to methods of using same in disease treatment.

BACKGROUND

The biological actions of estrogens and antiestrogens are manifest through two distinct high affinity receptors, estrogen receptor α (ERα) and estrogen receptor β (ERβ) (Kuiper et al, Proc. Natl. Acad. Sci. USA 93:5925 (1996), Mosselman et al, FEBS Lett. 392:49 (1996)). Estrogens are potent activators of both receptor subtypes and, with respect to ERα are known to play a critical role in the development and progression of ERα positive breast cancers. In this regard, antiestrogens, such as tamoxifen, which compete with estrogen for binding to the receptor effectively inhibit the growth of breast tumor cells (Katzenellenbogen et al, Breast Cancer Res. Treat. 44:23 (1997)). However, these cells ultimately become refractory to antiestrogen therapy, an event that is believed to stem from the ability of tamoxifen and other antiestrogens to display tissue selective agonist activity (Bertelli et al, Breast Cancer Res. Treat. 12:307 (1988), Love et al, New Engl. J. Med. 326:852 (1992), Kedar et al, Lancet 343:1318 (1994)). In particular, tamoxifen, which is an effective antagonist of ERα action in the breast, is a partial ERα agonist in the uterus, bone and cardiovascular systems (Bertelli et al, Breast Cancer Res. Treat. 12:307 (1988), Love et al, New Engl. J. Med. 326:852 (1992), Kedar et al, Lancet 343:1318 (1994)). These findings have led to the reclassification of tamoxifen and other antiestrogens as selective estrogen receptor modulators (SERMs) (Sato et al, FASEB J. 10:905 (1996)).

The molecular mechanism underlying the tissue restricted agonist activity of SERMs remains elusive. However, it is widely believed that a complex network of tissue specific co-regulatory proteins determines this specificity. Recent studies have identified a multitude of protein factors that interact with and modify the transcriptional activity of the C-terminal ligand-inducible activation function-2 (AF-2) (Robyr et al, Mol. Endocrinol. 14:329 (2000)). Relatively little is known about how the N-terminal activation function-1 (AF-1) signals. The present invention is based, at least in part, on the isolation of a novel ERα co-regulator that interacts with the ERα N-terminal domain. In particular, this protein, denoted RTA, for repressor of tamoxifen transcriptional activity, specifically inhibits tamoxifen mediated partial agonist activity. The identification of RTA makes possible methods of screening compounds for their use in the treatment of estrogen dependent diseases and disorders.

SUMMARY OF THE INVENTION

The invention relates to an estrogen receptor co-regulator and to antibodies specific therefor. The invention further relates to methods of screening test compounds for their suitability as estrogen receptor modulators and to methods of using same in disease treatment.

Objects and advantages of the present invention will be clear from the description that follows.

BRIEF DESCRIPTION OF THE DRAWINGS

(FIG. 2A) GST alone or GST fusion protein, GST-RTA, was isolated from bacteria and immobilized on glutathione-sepharose beads. In vitro translated [$^{35}$S] methionine labeled ERα or ERβ (FIG. 2A(a)) was incubated with the GST fusion proteins in binding buffer overnight at 4° C. Hormone (100 nM) was included in the binding buffer as indicated. NH=no hormone, E2=17-β-estradiol, and OT=4-hydroxy-tamoxifen. Bound proteins were eluted in SDS/PAGE sample buffer and were analyzed by SDS/PAGE. 1/10 input [$^{35}$S] methionine labeled protein is included as control. (FIG. 2B) GST alone, GST-ER-N-term (amino acids 1–182) or GST-ER-HBD (amino acids 282–595) proteins were isolated from bacteria and purified with glutathione-sepharose beads. In vitro translated RTA was incubated with the GST fusion proteins and analyzed as above. (FIG. 2C) HeLa cells were transfected with expression vectors for ERα and c-Myc tagged RTA together (lanes 1–2) or alone (lanes 3–4). Following transfection, cells were lysed and immunoprecipitated with mouse IgG (lane 1) or anti c-Myc monoclonal antibody (lanes 2–4). Reactions were washed 6× with lysis buffer, subjected to SDS/PAGE, and immunoblotted with anti-ERα monoclonal antibody H222. Mouse IgG heavy chain cross-reacts with secondary anti-rat IgG and is indicated.

(FIG. 3A) HeLa cells (top panels (a) and (b)) or HepG2 cells (lower panels (c) and (d)) were transfected with either the 1X-ERE-tata-Luc or C3-Luc reporter genes along with the ERα expression plasmid (pRST7-ERα). RTA expression plasmid (pCDNA-5XM-RTA) or control plasmid (PCDNA-5XM) was transfected as indicated. PCMV-β-Gal was included as internal control. Transfections contained 2200 ng reporter gene, 500 ng ERα expression plasmid, 100 ng pCMV-β-Gal, and 200 ng of either RTA or control plasmid. Cells were induced with ligand as indicated. Data for HeLa cells is presented as normalized response, which was obtained by dividing the luciferase activity by β-galactosidase activity. Data for HepG2 is presented as fold induction, which was obtained by dividing the normalized response in the presence of ligand by that in the absence of ligand. Transfections were performed in triplicate and error bars are presented as standard error of the mean (SEM). (FIG. 3B) HeLa cells were transfected as above with ERβ expression plasmid pRST7-ERβ and transcriptional activity was analyzed using the 1X-ERE-tata-Luc reporter. (FIG. 3C) RTA is not a general transcriptional repressor. HeLa cells were transfected with 100 ng pCMV-β-Gal and 2700 ng empty expression plasmid (pRST7) in addition to either RTA expression or control plasmid (200 ng). β-galactosidase activity was measured after 48 hrs. Data was normalized to protein concentration and presented as relative β-galactosidase activity. Error bars are presented as above. (FIG. 3D) RTA contains autonomous repressor activity. HepG2 cells were transfected with either pM (control), pM-NCoR or pM-RTA (500 ng) in addition to either 5X-Gal4-tata-Luc or TK-Gal4-Luc (2400 ng) (Digesting pCDNA-5XM-RTA with BamHI/XbaI and subsequent subcloning of resultant DNA into pM (Clontech) created pM-RTA. 5X-Gal4-tata-Luc is described elsewhere (Norris et al, Science 285:744 (1999)). Transfections were performed in triplicate and data is presented as above.

FIGS. 4A–4E. RTA repressor activity is mediated by the RNA recognition motif. HeLa cells were transfected with either (FIG. 4A) 1X-ERE-tata-Luc or (FIG. 4B) 3X-ERE-tata-Luc (2200 ng) along with pRST7-Erα (500 ng) and the indicated RTA expression plasmid (200 ng) (pCDNA-5XM-RTA-N (amino acids 1–223), pCDNA-5XM-RTA-C (amino acids 224–390), pCDNA-5XM-RTA-Δ2 (deletion amino acids 123–128) and pCDNA-5XM-RTA-Δ1 (deletion amino acids 160–167) were created by PCR using RTA cDNA as template. Resultant DNA was subcloned into pCDNA-5XM). Shown in (FIG. 4A) is schematic representation of RTA mutants. Cells were induced with ligand (10 nM) as indicated. ICI=ICI 182, 780. Transfections were performed in triplicate and error is presented as standard error of the mean (SEM). (FIG. 4C) HeLa cells were transfected with the 3X-ERE-tata-Luc reporter gene along with the RTA-Δ2 expression plasmid. Cells were induced with ligand (10 nM) as indicated. 5638=GW5638, Ralox=raloxifene, Nafox=nafoxidene, Idox=Idoxifene. (FIG. 4D) De-repression of AF-1 by RTA-Δ2 converts antagonists into agonists. HeLa cells were transfected with the 3X-ERE-tata-Luc reporter plasmid (2200 ng) along with RTA-Δ2 (200 ng) and the indicated ERα expression plasmid (500 ng) (ERα expression vectors TAF1-3X, TAF2, ER-LL and ER-351 are described elsewhere (Tzuckerman et al, Mol., Endocrinol. 8:21 (1994), Norris et al, Mol. Endocrinol. 11:747 (1997), Norris et al, J. Biol. Chem. 273:6679 (1998)). TAF1-3X contains amino acid substitutions of D538N, E542Q, and D545N. ER-LL contains amino acid substitutions of L540A, L541A. Cells were induced with ligand (10 nM) as indicated. Error is presented as before. (FIG. 4E) RNA homopolymer binding assay. Binding of p(A), p(C), p(G) and p(U) ribonucleic acids to RTA, RTA-Δ2, RTA-C and luciferase (Luc) is shown. 10% input is included for reference.

DETAILED DESCRIPTION OF THE INVENTION

The present invention relates generally to a heterogeneous nuclear ribonucleoprotein (hnRNP) designated RTA (repressor of tamoxifen transcriptional activity). RTA contains an RNA recognition motif (RRM) and interacts with the N-terminal activation domain of estrogen receptor α (ERα). RTA interacts with RNA in vitro and its over-expression inhibits the partial agonist activity manifest by the antiestrogen tamoxifen. As shown in the Example that follows, mutation of the RRM of RTA disrupts RNA binding and results in a dominant negative form of RTA that leads to de-repression of ERα transcriptional activity allowing all classes of antiestrogens to manifest partial agonist activity and enhancing agonist efficacy.

RTA Protein, Encoding Sequence, Methods of Production and Anti-RTA Antibodies

Figure 1:
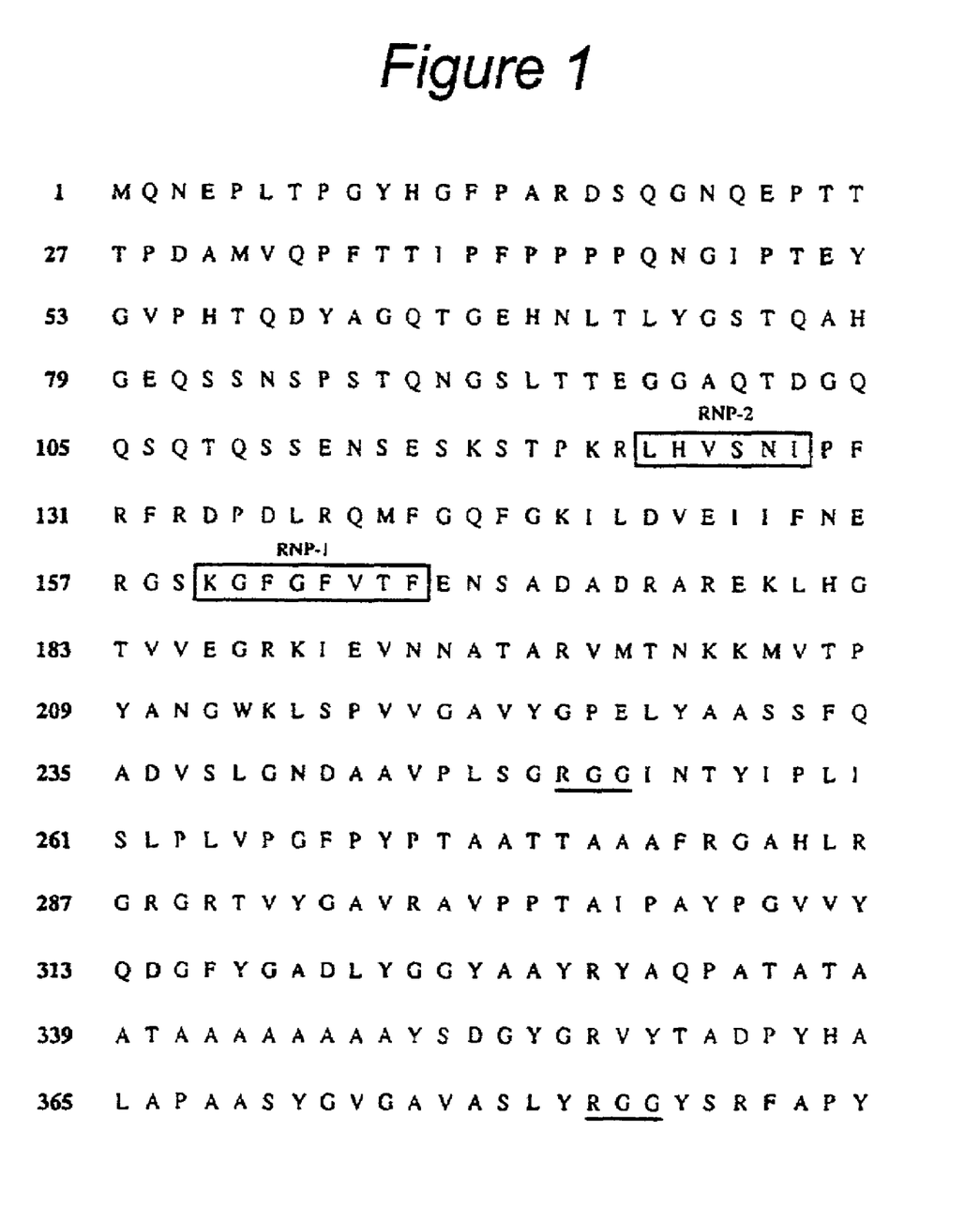
FIG. 1. Amino acid sequence of RTA (SEQ ID NO:1). RTA comprises a 390 amino acid protein. It contains an RNA recognition motif (RRM), which consists of two ribonucleoprotein (RNP) domains and the sequences spanning them. RNP-2 (6 amino acids) and RNP-1 (8 amino acids) are shown boxed. These domains along with the arginine/glycine (RGG) rich sequences (underlined) are common structural features of RNA binding proteins.

The present invention relates to nucleotide sequences that encode the amino acid sequence of the mammalian RTA protein, particularly, the human RTA protein, or portions thereof of at least 5 amino acids, preferably at least 10 amino acids more preferably, at least 50 amino acids and most preferably, at least 100, 150, 200, 250, 300 or 350 amino acids. In particular, the present invention relates to nucleotide sequences that encode the amino acid sequence given in FIG. 1, or portions thereof as defined above. Further, nucleotide sequences to which the invention relates include those encoding substantially the same protein as shown in FIG. 1, for example, inter- and intraspecies variations thereof, as well as proteins that differ from that shown in FIG. 1 in having one or more conservative substitutions (e.g., one small aliphatic, nonpolar or slightly polar residue substituted for another (i.e., Ala/Ser/Thr/Pro/Gly), one negatively charged residue or its amide substituted for another (i.e., Asp/Glu/Gln), one positively charged residue substituted for another (i.e., His/Arg/Lys), one large aliphatic nonpolar residue substituted for another (i.e., Met/Ile/Leu/Val/Cys), or one large aromatic residue substituted for another (i.e., Phe/Tyr/Trp)), which proetins can be functional equivalents of that shown in FIG. 1. The invention also relates to nucleic acids complementary to those described above.

The present invention also relates to a recombinant molecule comprising a nucleotide sequence as described above and to a host cell transformed therewith. Using standard methodologies, well known in the art, a recombinant molecule comprising a vector and a nucleotide sequence encoding, for example, the RTA protein, or portion thereof as defined above, can be constructed. Vectors suitable for use in the present invention include plasmid and viral vectors (e.g., adenoviral expression vectors). Plasmid vectors into which an encoding sequence can be cloned include any vectors compatible with transformation into a selected host cell. Such vectors include pcDNA3 and pM. The nucleotide sequence of the invention can be present in the vector operably linked to regulatory elements, for example, a promoter. Suitable promoters include, but are not limited to CMV, TK, SV40, adenoviral and retroviral promoters.

As indicated above, the recombinant molecule of the invention can be constructed so as to be suitable for transforming a host cell. Suitable host cells include prokaryotic cells, such as bacteria, lower eukaryotic cells, such as yeast, and higher eucaryotic cells, such as mammalian cells, and insect cells. The recombinant molecule of the invention can be introduced into appropriate host cells by one skilled in the art using a variety of known methods.

The present invention further relates to a method of producing RTA protein, or portions thereof, as defined above. The method comprises culturing the above-described transformed host cells under conditions such that the encoding sequence is expressed and the protein thereby produced.

The nucleic acid sequence(s) of the invention can be used, in accordance with standard protocols, as probes and primers. As such, portions of the RTA encoding sequence can be used.

The present invention further relates to the mammalian RTA protein, particularly, the human RTA protein, substantially free of proteins with which it is normally associated, or portions thereof as defined above, and to proteins substantially similar to that shown in FIG. 1, including proteins that differ therefrom in having one or more conservative substitutions. The proteins, polypeptides and peptides of the invention can be produced recombinantly using the nucleic acid sequences as described above, or chemically using known methods. The protein of the invention can be produced alone or as a fusion product, for example, with a protein such as β-galactosidase, gal4 DNA binding domain and green fluorescent protein. Such fusion products can be produced recombinantly. For example, the coding sequence of the invention (eg the sequence encoding the mammalian RTA protein) can be cloned in frame with a sequence encoding another protein (such as β-galactosidase) and the fusion product expressed in an appropriate host cell.

The proteins, polypeptides and peptides of the invention can be used as antigens to generate RTA specific antibodies. Methods of antibody generation are well known in the art. Both monoclonal and polyclonal antibodies are included within the scope of the invention, as are binding fragments thereof. Also included are chimeric and humanized antibodies. One skilled in the art will appreciate that such antibodies can be used to selectively identify and isolate the RTA protein and portions thereof.

Compound Screens

The present invention also relates to methods of screening test compounds for their ability to serve as modulators of ER activity. The present methods can be used to screen for novel SERMS or "complete" antiestrogens, that is ER antagonists that do not activate ER in the presence of RTA mutants (e.g., RTA Δ2 and RTA-C described in the Example that follows) that co-activate ER transcriptional activity in the presence of currently available SERMS. Compounds so identified can be used to treat a variety of estrogen-dependent diseases, including breast cancer (e.g., primary ER positive breast tumors as well as ER positive breast tumors characterized by resistance to various ER modulators). The present methods can also be used to screen compounds for their suitability for use in treating a variety of disorders or conditions of the bone (e.g. osteoporosis) and the cardiovascular system as well as neurological diseases/disorders, including Alzheimer's disease, and neuroendocrine disorders such as hot flashes.

In order to identify novel SERMS or "complete" antiestrogens, it is useful to prescreen test compounds for their ability to bind ER. Such prescreens can be conducted using any of a variety of standard binding assays. Test compounds that are found to bind ER can then be further screened in a cell-based assay. One such cell-based assay involves the use of a cell (e.g. a HELA cell) into which has been introduced: i) a construct (e.g. a plasmid) comprising DNA encoding the ERα isoform, ii) a construct (e.g. a plasmid) comprising DNA encoding a RTA mutant that co-activates ER transcriptional activity in the presence of currently available SERMS (e.g., RTA-Δ2 or RTA-C) and iii) a construct comprising an ER response element, a promoter and a reporter gene, in operable linkage (e.g., 3X-ERE-tata-Luc). A normalization vector (e.g., pCMVβGal) can also be used. Test compounds, e.g., those found to bind ER, can be contacted with the cell and the level of ER activation determined. Test compounds that give low to no level of activation (relative to known modulators such as ICI, tamoxifen and estradiol) (e.g., those that show at least a 75% lower level) can be predicted to be useful in treating the diseases and disorders described above.

Pharmaceutical Compositions

The present invention also relates to pharmaceutical compositions comprising, as active agent, the proteins, peptides, nucleic acids or antibodies of the invention. The invention also relates to compositions comprising, as active agent, compounds selected using the above-described screening protocols. Such compositions include the active agent in combination with a pharmaceutically acceptable carrier. The amount of active agent in the composition can vary with the agent, the patient and the effect sought. Likewise, the dosing regimen will vary depending on the composition and the disease/disorder to be treated.

Detection/Diagnosis:

The present invention further relates to methods detecting levels of wild type RTA in a sample from a patient, (e.g., a breast cancer patient). In one such method, a sample of tumor (e.g., a tumor extract or tumor slice) is contacted with anti-RTA antibodies, for example, labelled with a detectable label (e.g., fluorophore, chromophore or isotope, etc)) under conditions such that the antibodies can bind to RTA present in the sample. The amount of antibody-bound RTA present in the sample can be determined, in the case of tumor extracts, using, for example, Western blots or ELISAs, and, in the case of tumor slices, using, for example, immunocytochemical techniques. In the case of tumors found to have relatively low levels of RTA, treatment with an antiestrogen may not indicated.

Certain aspects of the invention can be described in greater detail in the non-limiting Example that follows.

EXAMPLE

To identify potential co-regulators that interact with the ERα N-terminal domain, a fragment of ERα was used containing amino acids (aa) 51–149 as bait in a yeast two-hybrid screen. (The yeast strain HF7C (Clontech) was transformed with pGBT9-ER N-term which expresses ER amino acids 51–149 fused to the Gal4 DBD along with a HeLa cell cDNA library fused to the Gal4 activation domain (AD) cloned in pACT2. HF7C contains two inducible reporter genes, His3 and β-galactosidase, both under control of a Gal4 upstream enhancer sequence. Cells were plated on yeast minimal media (MM) lacking histidine plus 5 mM aminotriazole (AT). ER N-terminal interacting clones were identified based on their ability to induce HIS3 expression. HIS3+ colonies were selected and analyzed for β-galactosidase expression using a filter lift assay. β-galactosidase positive colonies were selected and the resultant HeLa cDNA was isolated and re-transformed into yeast strain Y190 (Clontech) for verification of β-galactosidase activity in liquid culture. Yeast bait expression plasmid GBT9-ER-N-term) was created by PCR using ERα cDNA as templae. Resultant DNA was subcloned into EcoRI/SalI site of parent vector (pGBT9, Clontech).) Two cDNAs from the same gene were identified whose corresponding proteins interact with the ERα N-terminal bait. The larger clone, RTA, was sequenced and was found to contain a large open reading frame encoding a protein of 390 aa (FIG. 1). This protein is highly homologous to a human cDNA clone, P83A20, and likely represents an alternatively spliced variant of that cDNA. Several homologues of RTA have been identified and include the human ataxin-2 binding protein 1 (A2BP1) and the Caenorhabditis elegans protein FOX-1 (Shibata et al, Hum. Mol. Genet. 9:1303 (2000), Skipper et al, Genetics 151:617 (1999)). The most notable sequence feature of RTA is the identification of a well-characterized RRM or RNA binding domain (RBD) (Burd et al, Science 265:615 (1994), Krecic et al, Curr. Opin. Cell Biol. 11:363 (1999)). This domain is characterized by the presence of two short stretches of 6 and 8 amino acids respectively termed RNP-2 and RNP-1 (FIG. 1). The sequence spanning the RNP domains includes residues that are critical for proper protein folding. Other notable features of RTA are the presence of a glutamine-rich N-terminal domain and an alanine-rich C-terminal domain. Unusual amino-acid distributions are common structural features of RNA binding proteins and are proposed to be involved in protein-protein interactions. RTA also contains two arginine/glycine rich (RGG) boxes (FIG. 1). These sequences are thought to be involved in binding RNA (Krecic et al, Curr. Opin. Cell Biol. 11:363 (1999)).

Figure 2A:
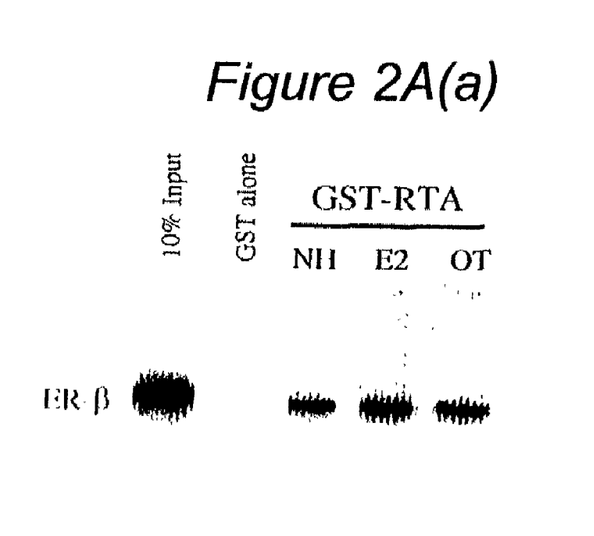
FIGS. 2A–2C. RTA interacts with ERα and ERβ in vitro.

A direct interaction between ERα and RTA was verified in vitro using a protein-protein interaction assay. (Glutathione-S-transferase (GST) pull-down assays were performed as follows. [$^{35}$S]methionine labeled ERα and ERβ were translated from pRST7-ERα and pRST7-ERβ respectively using Promega in vitro TNA rabbit reticulocyte lysate kit as described in manufacturers protocol. PGEX-5X-1 (GST alone) (Amersham Pharmacia Biotech) and pGEX-5X-RTA (GST-RTA) were transformed into bacterial strain BL-21 (Stratagene) and proteins were purified with glutathione-sepharose beads (Amersham Pharmacia Biotech). Resultant labeled proteins were combined with GST fusion proteins in 1 mL NETN binding buffer (50 mM NaCl, 1 mM EDTA pH8.0, 20 mM Tris pH 8.0, 0.5% NP-40) and incubated overnight at 4° C. Beads were washed in washing buffer (NETN, 100 mM NaCl) 5 times and binding proteins were eluted by boiling in SDS sample buffer and analyzed by SDS/PAGE. Analysis of [$^{35}$S]methionine labeled RTA (pCDNA-RTA) binding to ER-HBD (HEI4G) and ER-N-Term (pGEX-5X-ER-N-Term) was performed as above. pRST7ERα and pRST7-ERβ were described elsewhere (Hall et al, Endocrinology 140:5566 (1999)). pCDNA3-RTA was created by PCR using TRA cDNA (pGal-GH-RTA, yeast two-hybrid AD fusion construct) as template. Resultant DNA was subcloned into BamHI/XhoI site of pCDNA3 (Stratagene). Digesting pCDNA3-RTA with BamHI/XhoI and subsequent subcloning of resultant DNA into pGEX-5X-1 created GST-RTA. GST-ER-N-term was created by PCR using ERα cDNA as template. Resultant DNA was subcloned into EcoRI/XhoI site of pGEX-5X-1. GST-ER-HBD (HEI4G) was described elsewhere (Sadovsky et al, Mol. Cell. Bio. 15:1554 (1995)). 17β-estradiol and 4-hydroxy-tamoxifen were purchased from Sigma Chemical Company.) As expected for an AF-1 interacting protein, RTA was found to interact with ERα in a ligand-independent manner (FIG. 2A). A marginal but reproducible increase in binding was found between RTA and the tamoxifen-ER complex. ERα did not interact with the control protein (GST alone). Similar to ERα, RTA demonstrates ligand-independent interactions with ERβ (FIG. 2A). This finding was somewhat unexpected since the N-terminal domains are not well conserved between the receptor isoforms. However, these data suggest that a common structural feature exists within the N-terminal domains of ERα and ERβ.

Figure 2B:
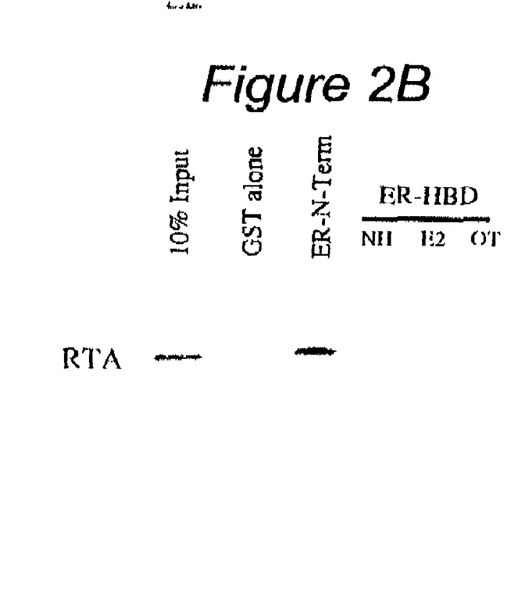
Figure 2C:
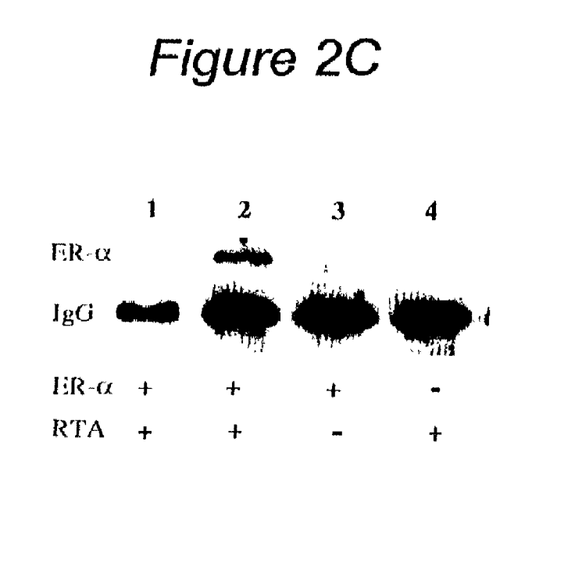

In order to determine which domains of ERα were responsible for binding RTA, interaction assays were performed between RTA and either ERα N-terminal or ERα hormone binding domain (HBD) GST fusion proteins. Consistent with the yeast two-hybrid results, RTA interacts with the N-terminal fragment of ERα in vitro (FIG. 2B). An interaction between RTA and the ER-HBD could not be detected under any conditions tested. Co-immunoprecipitation experiments were performed to determine if an interaction could be detected between ERα and c-Myc-tagged RTA in cells. (HeLa cells were cultured in tissue-culture dishes at 2.0×106 cells per plate in minimal essential media (MEM) (Life Technologies) containing 10% FETAL BOVINE SERUM (fbs) (Life Technologies). Cells were transfected as described elsewhere (Norris et al, J. Biol. Chem. 273:6679 (1998)) with pRST7-ERα and pCDNA-5XM-RTA (c-Myc tagged RTA) either individually or in combination. Following transfection, cells were cultured in MEM/FBS containing 0.1 μM 4-hydroxy-tamoxifen for 24 hrs. Cells were washed with PBS and 0.5 ml lysis buffer (PBS, 0.5% tritonX, protease inhibitors) was added to the plates. Lysate was precleared with 50 μl protein A sepharose beads (Zymed) and mouse IgG for 2 hrs at 4C. Either anti c-Myc monoclonal antibody 9E10 (Santa Cruz Biotechnology) or anti mouse IgG was then added for 2 hrs at 4° C. 40 μl of protein A beads was then added to the antibody/lysate mixture for an additional hr at 4° C. Beads were washed 6 times with lysis buffer and resuspended in SDS/PAGE sample buffer. Proteins were resolved on 10% SDS-PAGE and transferred to nitrocellulose membranes and probed with monoclonal antibody H222. Complexes were detected using ECL following manufacturer's protocol (Amersham Pharmacia Biotech). pCNDA A-5XM-RTA was created by PCR using TRA cDNA as template. Resultant DNA was subcloned into pCDNA-5XM digested with BamHI/XbaI.) ERα was efficiently immunoprecipitated as a complex with RTA only in the presence of an antibody specific for c-Myc and not mouse IgG alone (FIG. 2C). Furthermore, transfection of either ERα or c-Myc-tagged RTA alone resulted in the failure to detect ERα in the immunoprecipitates. These data demonstrate that ERα and RTA form a complex within the environment of the cell.

Figure 3A:
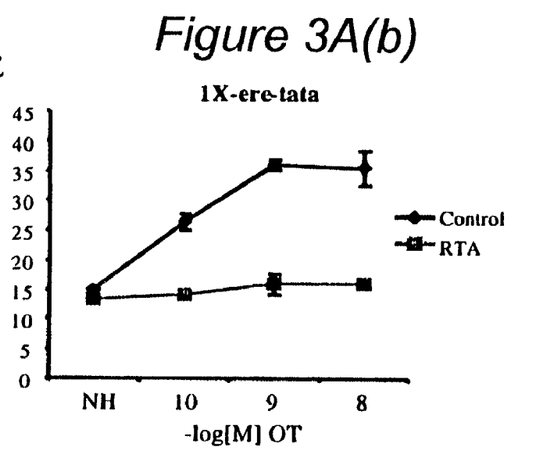
FIGS. 3A–3D. RTA is a novel co-regulator of ER signaling.

To address the question of whether RTA is a co-regulator of ERα transcriptional activity, the effect of RTA expression on ERα mediated transcriptional activity was examined. (HepG2 or HeLa cells were cultured in 24 well plates overnight in phenol red free MEM (Life Technologies) plus 10% charcoal/dextran treated fetal bovine serum (Hyclone Inc). Cells were transfected as described above. IX-ERE-tata-Luc, C3-Luc and pCMV-β-gal were described elsewhere (Norris et al, Science 285:744 (1999)).) Both estrogen and tamoxifen activate the 1X-ERE-tata-Luc reporter gene in HeLa cells transfected with ERα (FIG. 3A, top panels). Expression of RTA had a minimal effect on estradiol-mediated transcription, inhibiting this activity by less than 10%. However, RTA completely inhibits tamoxifen-mediated transcription indicating that RTA is a novel co-repressor of ERα signaling. Concordant with the results obtained in HeLa cells, RTA was found to be a potent but specific repressor of tamoxifen mediated transcription in HepG2 cells (FIG. 3A, lower panels).

Figure 3B:
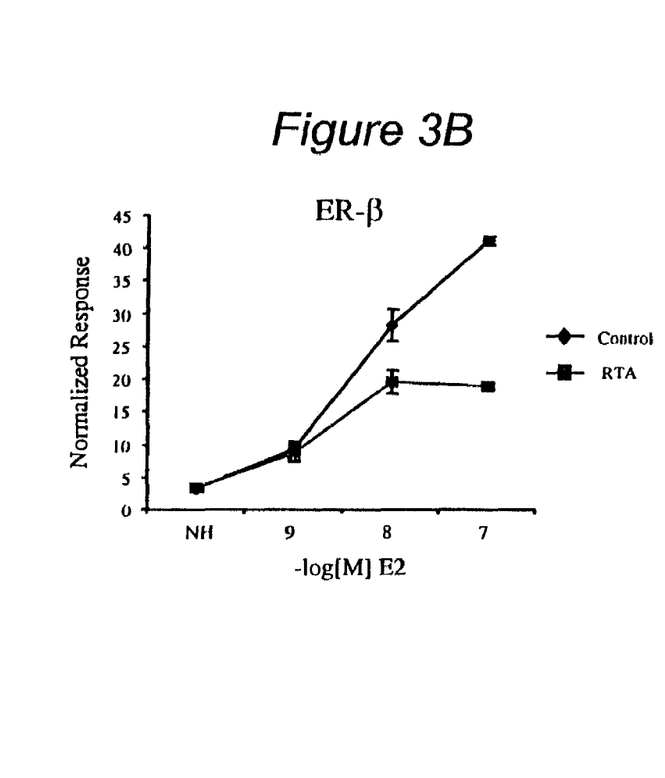

The result of the in vitro interaction assays indicate that RTA interacts with ERβ in a manner similar to Erα suggesting that RTA may have an effect on ERβ signaling. In contrast to Erα, estradiol activated ERβ transcriptional activity is inhibited by the expression of exogenous RTA (FIG. 3B). It has been shown previously that ERβ contains a repressor domain in the N-terminus of the receptor (Hall et al, Endocrinology 140:5566 (1999)). A strong association between RTA and ERβ may account for this repression.

Figure 3C:
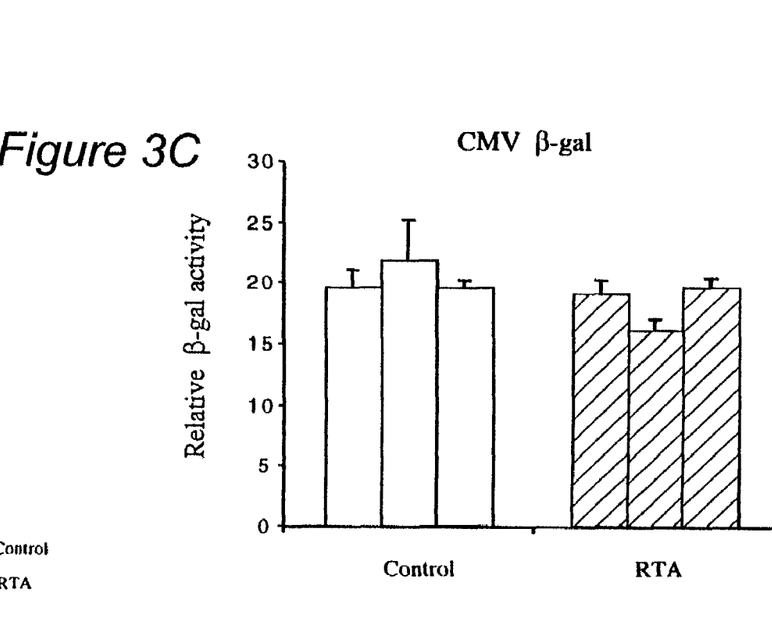

Although RTA specifically inhibits tamoxifen but not estradiol activated ERα transcriptional activity suggesting that RTA is not a general repressor of transcription, it was of interest to determine if RTA was capable of inhibiting other unrelated transcription factors. To this end, it was possible to show that expression of RTA had no effect on the transcriptional activity of the complex CMV viral promoter confirming its functional specificity (FIG. 3C).

Figure 3D:
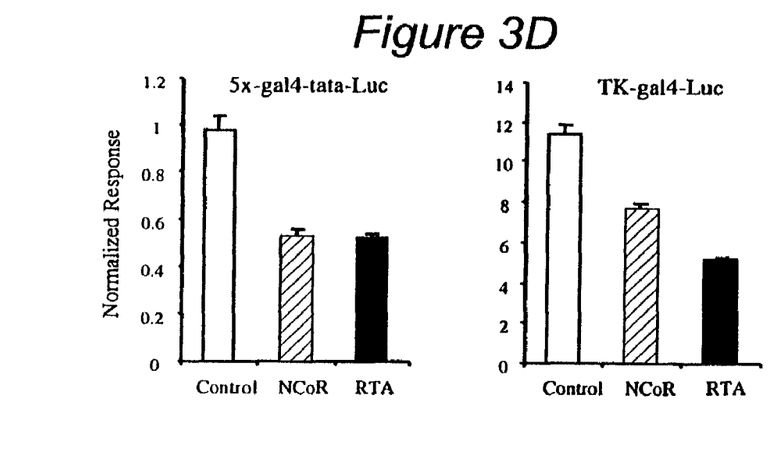

The results indicate that RTA is a potent repressor of ERα-mediated transcriptional activity. However, RTA does not induce receptor turnover nor does it interfere with the DNA binding activity of the receptor. Therefore, it was considered that RTA may function as a repressor in a manner similar to REA (repressor of estrogen receptor activity) (Montano et al, Proc. Natl. Acad. Sci USA 96:6947 (1999)) by competing with co-activator binding to the receptor or alternatively it may contain an autonomous repressor domain. In order to determine if RTA contains an autonomous transcriptional repressor domain, RTA was fused to the Gal4 DBD and the transcriptional activity of this modified protein tested using two distinct Gal4-responsive reporter genes (FIG. 3D). For comparison using this assay, the transcriptional activity of a known transcriptional repressor, nuclear receptor co-repressor (NCoR) was also analyzed (Alland et al, Nature 387:49 (1997)). RTA and NCoR inhibit the transcriptional activity of both reporter genes. Interestingly, RTA was at least as efficacious as NCoR under these conditions. These data suggest that the repressor function of RTA can be ascribed at least in part to the presence of an autonomous repressor domain.

Figure 4A:
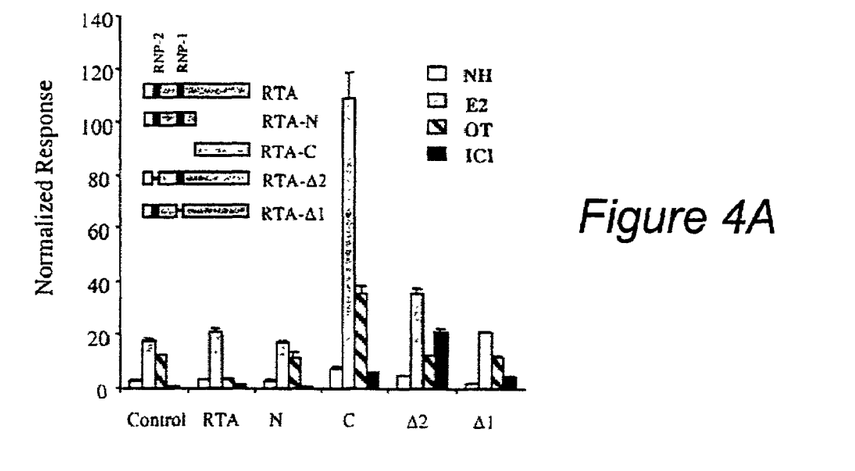
Figure 4B:
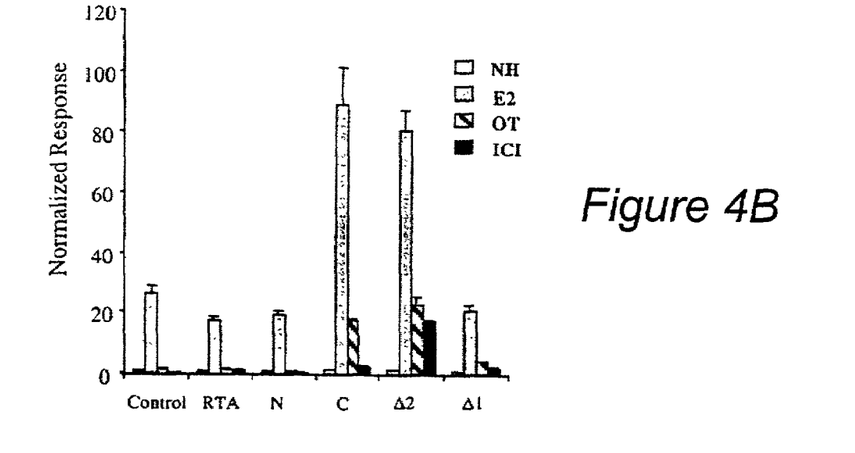
Figure 4C:
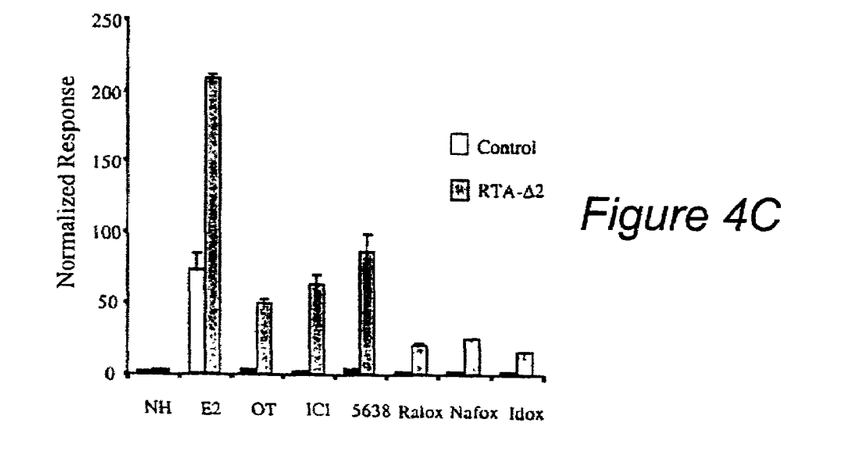

To investigate the domains or sequences within RTA required for repressor activity, several RTA mutants were created and tested for their ability to inhibit ERα mediated transcriptional activity on the 1X-ERE-tata-Luc (FIG. 4A) or 3X-ERE-tata-Luc (FIG. 4B) reporter genes. As expected, RTA inhibits the partial agonist activity of tamoxifen manifest on the 1X-ERE-tata-Luc-reporter gene (FIG. 4A). A C-terminal deletion mutant of RTA (RTA-N) containing amino acids 1–223 has no effect on ERα signaling in this context demonstrating that the C-terminal domain of RTA is required for repressor activity. Since the C-terminal fragment of RTA was isolated in the yeast two-hybrid screen, this domain likely mediates the interaction between ERα and RTA. Removal of the RRM (RTA-C) or deletion of either RNP domain (RTA-Δ2 and RTA-Δ1) leads to loss of repressor function. These results clearly demonstrate the importance of the RRM in mediating the repressor activity of RTA. Expression of RTA-C enhances both estradiol and tamoxifen mediated transcription suggesting that this mutant acts in a dominant-negative manner to relieve the repressive activity of endogenous RTA (FIG. 4A). Remarkably, expression of RTA-Δ2 converts the pure antagonist ICI 182,780 into an agonist. Similar results were obtained when the repressor function of the RTA mutants was analyzed using the 3X-ERE-tata-Luc-reporter gene (FIG. 4B). Expression of RTA-C converts tamoxifen into a powerful agonist while expression of RTA-Δ2 converts both tamoxifen and ICI 182,780 into agonists (FIG. 4B). The ability of RTA-Δ2 to alter the pharmacology of ER ligands was not limited to tamoxifen and ICI 182,780 as all SERMs demonstrate agonist activity when this mutant is expressed (FIG. 4C). Taken together, these results indicate that RTA acts to repress ERα transcriptional activity. Mutant forms of RTA, which lack a functional RRM, operate to block the repressive activity of endogenous RTA. Differences in the expression of RTA or a related protein may explain the tissue selective agonist/antagonist activity of SERMs.

Figure 4D:
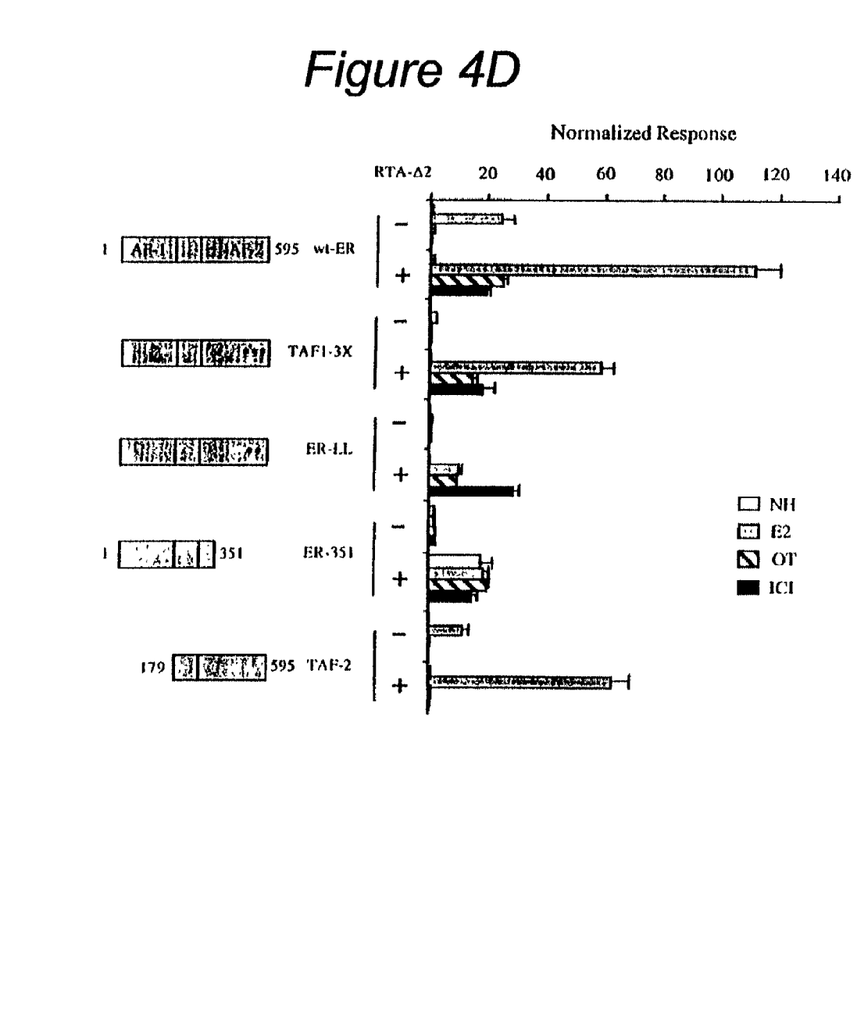

It was next of interest in determining how RTA-Δ2 alters the pharmacology of antiestrogens on ERα signaling. To accomplish this, the transcriptional activity of several ERα mutants was analyzed in the presence and absence of RTA-Δ2 (FIG. 4D). ERα contains two primary activation domains, AF-1 and AF-2, whose transcriptional activity is manifest in a cell- and promoter-specific manner (Berry et al, EMBO J. 9:2811 (1990), Tzuckerman et al, Mol., Endocrinol. 8:21 (1994)). AF-2 is embedded within the receptor HBD and its transcriptional activity is modulated by ligand-induced conformational changes. AF-1 is a constitutive activator. Although they function independently, full ERα transcriptional activity typically requires the presence of both AFs. Mutants either lacking AF-2 (ER-351) or containing point mutations which destabilize AF-2 (TAF1-3X, ER-LL) are transcriptionally inactive in most environments (Tzuckerman et al, Mol., Endocrinol. 8:21 (1994), Norris et al, Mol. Endocrinol. 11:747 (1997), Norris et al, J. Biol. Chem. 273:6679 (1998)). These mutants, with the exception of ER-351, bind hormone similar to wt-ERα. Furthermore, they all contain functional AF-1 domains whose activity is somehow silenced. Remarkably, even for mutants that contain a completely disabled AF-2 domain (ER-LL, ER-351), expression of RTA-Δ2 restores their transcriptional activity and allows antiestrogens to be recognized as ERα-agonists (FIG. 4D). These results demonstrate that when the repressor function of RTA is blocked, the need for a functional AF-2 is bypassed. RTA-Δ2 also enhanced TAF-2 transcriptional activity suggesting that RTA can interact with the receptor HBD either directly or indirectly. Although it was not possible to detect an interaction between RTA and ERα-HBD in vitro, studies with SRC-1 and other co-regulatory proteins indicate that they typically interact with both the receptor N- and C-terminal domains suggesting that this may be a common occurrence (Webb et al, Mol. Endocrinol 12:1605 (1998)). Taken together, these results demonstrate that when ERα is bound by antagonist, RTA functions to suppress the constitutive activity of the AF-1 activator. RTA-Δ2 acts in a dominant-negative manner to de-repress AF-1 activity. When bound by agonist, AF-2 functions to overcome the repressive effect of RTA. Therefore, RTA over-expression has only a marginal effect on estradiol activated transcription. These results are similar to previous studies from our laboratory that identified SSN6/TUP1 as a negative regulator of AF-1 function in yeast (McDonnell et al, Proc. Natl. Acad. Sci. USA 89:10563 (1992)). This complex is believed to function at the level of chromatin to suppress transcription (Watson et al, Genes Dev. 14:2737 (2000)). Sequence comparisons between RTA and SSN6/TUP1 did not reveal any similarities; however, their functional characteristics suggest that they may operate in a similar manner.

Figure 4E:
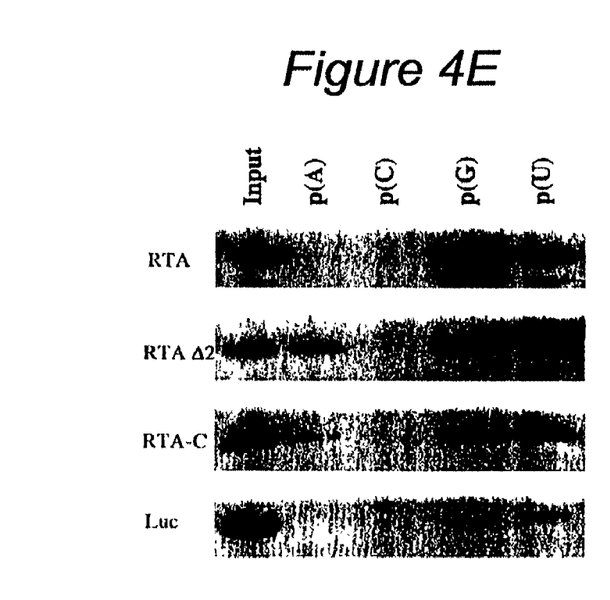

The results indicates that RNA binding is an important factor in the repressor function of RTA. Using an RNA homopolymer binding assay, a determination was made as to whether RTA interacts directly with RNA (28). RTA interacts strongly with p(G) and p(U) but not with p(A) or p(C) (FIG. 4E). RTA-Δ2 demonstrates a decrease in binding affinity for p(G) and an increase affinity for p(A). RTA-C interacts with p(U) but only weakly binds p(G). These results indicate that the ability of RTA to interact with RNA is an important determinant of the repressor function of RTA. Furthermore, there appears to be a correlation between the dominant negative transcriptional phenotype of the RTA mutants and disruption or alteration of RNA binding specificity.

All documents cited above are hereby incorporated in their entirety by reference.

What is claimed is:

1. An isolated nucleic acid encoding a mammalian repressor of tamoxifen transcriptional activity (RTA) protein, wherein said RTA protein has the amino acid sequence set forth in FIG. 1 (SEQ ID NO:1).

2. A vector comprising said nucleic acid according to claim 1.

3. The according to claim 2 further comprising a vector promoter operably linked to said nucleic acid.

4. An isolated host cell comprising said vector according to claim 2.

5. A method of producing a mammalian RTA protein comprising culturing said host cell according to claim 4 under conditions such that said nucleic acid is expressed and said mammalian RTA protein is thereby produced.

6. An isolated nucleic acid encoding a mutant of a human RTA protein, wherein said human RTA protein has the amino acid sequence of SEQ ID NO: 1 and wherein said mutant of said human RTA protein is devoid of RNP domain-2 at amino acids 123–128 of SEQ ID NO:1.

7. A vector comprising said nucleic acid according to claim 6.

8. The vector according to claim 7 further comprising a promoter operably linked to said nucleic acid.

9. An isolated host cell comprising said vector according to claim 7.

10. A method of producing a mutant of a human RTA protein comprising culturing the host cell according to claim 9 under conditions such that said nucleic acid is expressed and said mutant of said human RTA protein is thereby produced.

* * * * *

SEQUENCE LISTING

<160> NUMBER OF SEQ ID NOS: 1

<210> SEQ ID NO 1
<211> LENGTH: 390
<212> TYPE: PRT
<213> ORGANISM: Artificial Sequence
<220> FEATURE:
<223> OTHER INFORMATION: Description of Artificial Sequence:Estrogen receptor coregulator

<400> SEQUENCE: 1

```
Met Gln Asn Glu Pro Leu Thr Pro Gly Tyr His Gly Phe Pro Ala Arg
 1               5                  10                  15

Asp Ser Gln Gly Asn Gln Glu Pro Thr Thr Thr Pro Asp Ala Met Val
                20                  25                  30

Gln Pro Phe Thr Thr Ile Pro Phe Pro Pro Pro Gln Asn Gly Ile
            35                  40                  45

Pro Thr Glu Tyr Gly Val Pro His Thr Gln Asp Tyr Ala Gly Gln Thr
        50                  55                  60

Gly Glu His Asn Leu Thr Leu Tyr Gly Ser Thr Gln Ala His Gly Glu
 65                  70                  75                  80

Gln Ser Ser Asn Ser Pro Ser Thr Gln Asn Gly Ser Leu Thr Thr Glu
                85                  90                  95

Gly Gly Ala Gln Thr Asp Gly Gln Gln Ser Gln Thr Gln Ser Ser Glu
            100                 105                 110

Asn Ser Glu Ser Lys Ser Thr Pro Lys Arg Leu His Val Ser Asn Ile
        115                 120                 125

Pro Phe Arg Phe Arg Asp Pro Asp Leu Arg Gln Met Phe Gly Gln Phe
    130                 135                 140

Gly Lys Ile Leu Asp Val Glu Ile Ile Phe Asn Glu Arg Gly Ser Lys
145                 150                 155                 160

Gly Phe Gly Phe Val Thr Phe Glu Asn Ser Ala Asp Ala Asp Arg Ala
                165                 170                 175

Arg Glu Lys Leu His Gly Thr Val Val Glu Gly Arg Lys Ile Glu Val
            180                 185                 190

Asn Asn Ala Thr Ala Arg Val Met Thr Asn Lys Lys Met Val Thr Pro
        195                 200                 205

Tyr Ala Asn Gly Trp Lys Leu Ser Pro Val Val Gly Ala Val Tyr Gly
    210                 215                 220

Pro Glu Leu Tyr Ala Ala Ser Ser Phe Gln Ala Asp Val Ser Leu Gly
225                 230                 235                 240

Asn Asp Ala Ala Val Pro Leu Ser Gly Arg Gly Gly Ile Asn Thr Tyr
                245                 250                 255

Ile Pro Leu Ile Ser Leu Pro Leu Val Pro Gly Phe Pro Tyr Pro Thr
            260                 265                 270

Ala Ala Thr Thr Ala Ala Ala Phe Arg Gly Ala His Leu Arg Gly Arg
        275                 280                 285

Gly Arg Thr Val Tyr Gly Ala Val Arg Ala Val Pro Thr Ala Ile
    290                 295                 300

Pro Ala Tyr Pro Gly Val Val Tyr Gln Asp Gly Phe Tyr Gly Ala Asp
305                 310                 315                 320

Leu Tyr Gly Gly Tyr Ala Ala Tyr Arg Tyr Ala Gln Pro Ala Thr Ala
                325                 330                 335

Thr Ala Ala Thr Ala Ala Ala Ala Ala Ala Ala Ala Tyr Ser Asp Gly
```

-continued

```
                   340                 345                 350
Tyr Gly Arg Val Tyr Thr Ala Asp Pro Tyr His Ala Leu Ala Pro Ala
        355                 360                 365

Ala Ser Tyr Gly Val Gly Ala Val Ala Ser Leu Tyr Arg Gly Gly Tyr
        370                 375                 380

Ser Arg Phe Ala Pro Tyr
385                 390
```